United States Patent [19]
Baumann et al.

[11] Patent Number: 5,840,722
[45] Date of Patent: Nov. 24, 1998

[54] USE OF CARBOXYLIC ACID DERIVATIVES AS DRUGS

[75] Inventors: Ernst Baumann, Dudenhofen; Uwe Josef Vogelbacher; Joachim Rheinheimer, both of Ludwigshafen; Dagmar Klinge, Heidelberg; Hartmut Riechers, Ludwigshafen; Burkhard Kröger, Limburgerhof; Siegfried Bialojan, Oftersheim; Claus Bollschweiler, Heidelberg; Wolfgang Wernet, Hassloch; Liliane Unger, Ludwigshafen; Manfred Raschack, Weisenheim, all of Germany

[73] Assignee: BASF Aktiengesellschaft, Ludwigshafen, Germany

[21] Appl. No.: 718,377

[22] PCT Filed: Mar. 23, 1995

[86] PCT No.: PCT/EP95/01099

§ 371 Date: Sep. 30, 1996

§ 102(e) Date: Sep. 30, 1996

[87] PCT Pub. No.: WO95/26716

PCT Pub. Date: Oct. 12, 1995

[30] Foreign Application Priority Data

Mar. 31, 1994 [DE] Germany .................. 44 11 225.4

[51] Int. Cl.$^6$ ..................................... A01N 43/66
[52] U.S. Cl. ............................. 514/241; 514/276
[58] Field of Search ..................... 514/241, 276

Primary Examiner—Russell Travers
Assistant Examiner—Dwayne C. Jones
Attorney, Agent, or Firm—Keil & Weinkauf

[57] ABSTRACT

A method of inhibiting endothelin receptors by administering to a patient a compound of the formula I

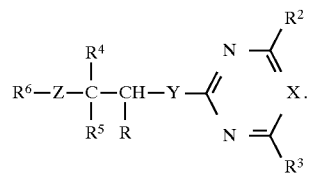

1 Claim, No Drawings

USE OF CARBOXYLIC ACID DERIVATIVES AS DRUGS

This application is a 371 of PCT/EP95/01094 filed on Mar. 23, 1995.

BACKGROUND OF THE INVENTION

The present invention relates to the use of certain carboxylic acid derivatives as drugs.

Endothelin is a peptide which is composed of 21 amino acids and which is synthesized and released by vascular endothelium. Endothelin exists in three isoforms, ET-1, ET-2 and ET-3. "Endothelin" or "ET" hereinafter means one or all isoforms of endothelin. Endothelin is a potent vasoconstrictor and has a potent effect on vascular tone. It is known that this vasoconstriction is caused by binding of endothelin to its receptor (Nature 332 (1988) 411–415; FEBS Letters 231 (1988) 440–444, and Biochem. Biophys. Res. Commun. 154 (1988) 868–875).

Increased or abnormal release of endothelin causes persistent vasoconstriction in peripheral, renal and cerebral vessels, which may lead to pathological states. It is reported in the literature that elevated plasma endothelin levels are found in patients with hypertension, acute myocardial infarct, pulmonary hypertension, Raynaud's syndrome or atherosclerosis and in the airways of asthmatics (Japan J. Hypertension 12 (1989) 79, J. Vascular Med. Biology 2 (1990) 207, J. Am. Med. Association 264 (1990) 2868).

Accordingly, substances -which specifically inhibit the binding of endothelin to the receptor should also antagonize the various physiological effects of endothelin mentioned above and therefore be valuable drugs.

SUMMARY OF THE INVENTION

We have found that certain carboxylic acid derivatives are good inhibitors of endothelin receptors.

The invention relates to the use of carboxylic acid derivatives with the formula I which is described hereinafter for the production of drugs, in particular for the production of inhibitors of endothelin receptors.

Carboxylic acid derivatives of the general formula I

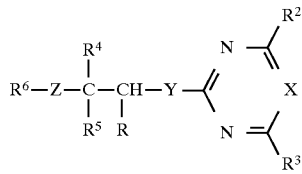

where R is formyl, $CO_2H$ or a radical which can be hydrolyzed to COOH, and the remaining substituents have the following meanings:

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{14}$ where $R^{14}$ is hydrogen or, together with $R^3$, forms a 3- or 4-membered alkylene or alkenylene chain in which, in each case, one methylene group is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $R^3$ is linked to $R^{14}$ as indicated above to form a 5- or 6-membered ring;

$R^4$ is $C_1$–$C_{10}$-alkyl which can carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxy-carbonyl, phenyl, phenoxy or phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_1$–$C_{10}$-alkyl which can carry from one to five halogen atoms and carries one of the following radicals: a five-membered heteroaromatic ring which contains from one to three nitrogen atoms and/or one sulfur or oxygen atom and which can carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and/or phenyl;

$C_3$–$C_2$-cycloalkyl or $C_3$–$C_2$-Cycloalkenyl, each of which can contain one oxygen or sulfur atom and can carry from one to five halogen atoms and/or one of the following radicals: $C_1$–$C_4$-alkyl, $C_1$–$C_4$-alkoxy, $C_1$–$C_4$-alkylthio, cyano, $C_1$–$C_8$-alkyl-carbonyl, $C_1$–$C_8$-alkoxycarbonyl, phenyl, phenoxy or phenyl-carbonyl, where the phenyl radicals in turn can carry from one to five halogen atoms and/or from one to three of the following radicals: $C_1$–$C_4$-alkyl, $C_1$–$C_4$-haloalkyl, $C_{l'}$–$C_4$-alkoxy, $C_1$–$C_4$-haloalkoxy and/or $C_1$–$C_4$-alkylthio; $C_3$–C6-alkenyl or $C_3$–$C_{46}$-alkynyl, each of which can carry from one to five halogen atoms and/or one of the following radicals; $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy o: phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

a five- or six-membered heteroaromatic ring which contains from one to three nitrogen atoms and/or one sulfur or oxygen atom and which can carry from one to four halogen atoms and/or one or two of the following radicals: $C_1$–$C_4$-alkyl, $C_{l'}$–$C_4$-haloalkyl, $C_1$–$C_4$-alkoxy, $C_1$–$c_4$-haloalkoxy, $C_1$–$C_4$-alkyl -thio, phenyl, phenoxy or phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_{1-4}$-haloalkoxy and/or $C_1$–$C_4$-alkylthio;

phenyl or naphthyl, each of which can be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, amino, $C_1$–$C_4$-alkyl-amino or $C_1$–$C_4$-dialkylamino;

$R^4$ and $R^5$ form, together with the adjacent carbon atom, a 3-to 8-membered ring which can contain one oxygen or sulfur atom and can carry from one to three of the following radicals; $C_1$–$C_4$-alkyl, halogen, $C_1$–$C_4$-haloalkyl, $C_1$–$C_4$-alkoxy, $C_1$–$C_4$-haloalkoxy and/or $C_1$–$C_4$-akylthio;

$R^5$ is hydrogen, $C_1$–$C_4$-alkyl, $C_3$–$C_6$-alkenyl, $C_3$–$C_4$-alkynyl, $C_3$–$C_5$-cycloalkyl, $C_1$–$C_4$-haloalkyl, $C_1$–$C_4$-alkoxyalkyl, $C_1$–$C_4$-alkylthioalkyl, phenyl or $R^5$ is linked to $R^4$ as indicated above to form a 3- to 8-membered ring;

$R^6$ is $C_1$–$C_8$-alkyl, $C_3$–$C_6$-alkenyl, $C_3$–$C_6$-alkynyl or $C_3$–$C_8$-cyclo-alkyl, it being possible for each of these radicals to be substituted one or more times by: halogen, nitro, cyano, $C_1$–$C_4$-alkoxy, $C_3$–$C_6$-alkenyloxy, $C_3$–$C_6$-alkynyloxy, $C_1$–$C_4$-alkyl-thio, $C_1$–$C_4$-haloalkoxy, $C_1$–$C_4$-alkylcarbonyl, $C_1$–$C_4$-alkoxy-carbonyl, $C_1$–$C_4$-alkylamino, di-$C_{l'}$–$C_4$-alkylamino, phenyl, phenoxy or phenyl which is substituted one or more times, e.g. from one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl or naphthyl, each of which can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1$–$C_4$-alkylamino or $C_1$–$C_4$-dialkylamino;

a five- or six-membered heteroaromatic ring which contains from one to three nitrogen atoms and/or one sulfur or oxygen atom and which can carry from one to four halogen atoms and/or one or two of the following radicals: $C_1$–$C_4$-alkyl, $C_1$–$C_4$-haloalkyl, $C_1$–$C_4$-alkoxy, $C_{14}$-haloalkoxy, $C_{14}$-alkyl-thio, phenyl, phenoxy or phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

Y is sulfur or oxygen or a single bond;

Z is sulfur or oxygen.

The compounds according to the invention are prepared starting from the epoxides IV which are obtained in a conventional manner, e.g. as described in J. March, Advanced Organic Chemistry, 2nd ed., 1983, p. 862 and p. 750, from the aldehydes or ketones II or the olefins III:

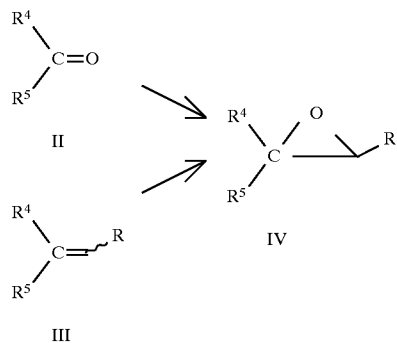

Carboxylic acid derivatives of the general formula VI can be prepared by reacting the epoxides of the general formula IV (e.g. with R=COOR$^{10}$) with alcohols or thiols of the general formula V where $R^6$ and Z have the meanings classified in claim 1.

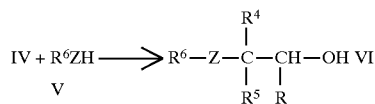

For this purpose, compounds of the general formula IV are heated with an excess of compounds of the formula V, e.g. 1.2–7, preferably 2–5, mole equivalents, at 50°–200° C., preferably 80°–150° C.

The reaction can also take place in the presence of a diluent. It is possible to use for this purpose all solvents which are inert to the reagents used.

Examples of such solvents or diluents are water, aliphatic, alicyclic and aromatic hydrocarbons, each of which may be chlorinated, such as hexane, cyclohexane, petroleum ether, naphtha, benzene, toluene, xylene, methylene chloride, chloroform, carbon tetrachloride, ethylene chloride and trichloroethylene, ethers such as diisopropyl ether, dibutyl ether, propylene oxide, dioxane and tetrahydrofuran, ketones such as acetone, methyl ethyl ketone, methyl isopropyl ketone and methyl isobutyl ketone, nitriles such as acetonitrile and propionitrile, alcohols such as methanol, ethanol, isopropanol, butanol and ethylene glycol, esters such as ethyl acetate and amyl acetate, acid amides such as dimethylformamide and dimethylacetamide, sulfoxides and sulfones, such as dimethyl sulfoxide and sulfolane, and bases such as pyridine.

The reaction is preferably carried out at from 0° C. to the boiling point of the solvent or mixture thereof.

The presence of a catalyst may be advantageous. Suitable catalysts for this purpose are strong organic and inorganic acids as well as Lewis acids. Examples thereof include sulfuric acid, hydrochloric acid, trifluoroacetic acid, boron trifluoride etherate and titanium(IV) alcoholates.

The compounds according to the invention where Y is oxygen and the remaining substituents have the meanings indicated for the general formula I can be prepared, for example, by reacting the carboxylic acid derivatives of the general formula VI in which the substituents have the stated meanings with compounds of the general formula VII

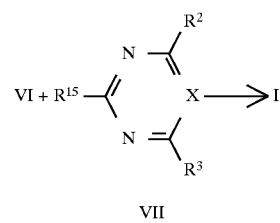

where $R^{15}$ is halogen or $R^{16}$–$SO_2$, where $R^{16}$ can be $C_1$–$C_4$-alkyl, $C_1$–$C_4$-haloalkyl or phenyl. The reaction preferably takes place in one of the abovementioned inert diluents with the addition of a suitable base, ie. a base which deprotonates the intermediate VI, at from room temperature to the boiling point of the solvent.

The base which can be used is an alkali metal or alkaline earth metal hydride such as sodium hydride, potassium hydride or calcium hydride or a carbonate such as an alkali metal carbonate, e.g. sodium or potassium carbonate, an alkali metal or alkaline earth metal hydroxide such as sodium or potassium hydroxide, an organometallic compound such as butyllithium or an alkali metal amide such as lithium diisopropylamide.

The compounds according to the invention where Y is sulfur and the remaining substituents have the meanings indicated for the general formula I can be prepared, for example, by reacting carboxylic acid derivatives of the general formula VIII, which can be obtained in a conventional manner from compounds of the general formula VI and in which the substituents have the above-mentioned meanings, with compounds of the general formula IX where $R^2$, $R^3$ and X have the meanings indicated for the general formula I.

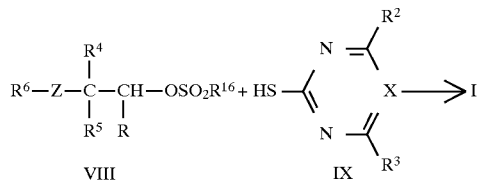

The reaction preferably takes place in one of the abovementioned inert diluents with the addition of a suitable base, i.e. a base which deprotonates the intermediate IX, at from room temperature to the boiling point of the solvent.

Besides the abovementioned bases it is also possible to use organic bases such as tertiary amines, e.g. triethylamine, pyridine, imidazole or diazabicycloandecene.

Compounds of the formula I can also be prepared by starting from the corresponding carboxylic acids, i.e. compounds of the formula I where $R^1$ is hydroxyl, and initially converting these in a conventional way into an activated form, such as a halide, an anhydride or imidazolide, and then reacting the latter with an appropriate hydroxyl compound HOR[10]. This reaction can be carried out in the conventional solvents and often requires addition of a base, in which case those mentioned above are suitable. These two steps can also be simplified, for example, by allowing the carboxylic acid to act on the hydroxyl compound in the presence of a dehydrating agent such as a carbodiimide.

Compounds of the formula I can also be prepared by starting from salts of the appropriate carboxylic acids, i.e. from compounds of the formula I where R is COR[1] and R[1] is OM where M can be an alkali metal cation or the equivalent of an alkaline earth metal cation. These salts can be reacted with many compounds of the formula R[1]-A where A is a conventional nucleofugic leaving group, for example halogen such as chlorine, bromine, iodine or aryl- or alkyl-sulfonyl which is unsubstituted or substituted by halogen, alkyl or haloalkyl, such as toluenesulfonyl and methylsulfonyl, or another equivalent leaving group. Compounds of the formula R—A with a reactive substituent A are known or can easily be obtained using general expert knowledge. This reaction can be carried out in the conventional solvents, advantageously with the addition of a base, those mentioned above being suitable.

The radical R in formula I can vary widely. R is, for example,

where R[1] has the following meanings:
a) hydrogen;
b) succinimidyloxy;
c) a 5-membered heteroaromatic ring linked via a nitrogen atom, such as pyrrolyl, pyrazolyl, imidazolyl and triazolyl, which can carry one or two halogen atoms, especially fluorine and chlorine and/or one or two of the following radicals:

$C_1$–$C_4$-alkyl such as methyl, ethyl, 1-propyl, 2-propyl, 2-methyl-2-propyl, 2-methyl-1-propyl, 1-butyl, 2-butyl; $C_1$–$C_4$-haloalkyl, in particular $C_1$–$C_2$-haloalkyl such as fluoromethyl, difluoromethyl, trifluoromethyl, chlorodifluoromethyl, dichlorofluoromethyl, trichloromethyl, 1-fluoroethyl, 2-fluoroethyl, 2, 2-fluoroethyl, 2,2,2-trifluoroethyl, 2-floro-2,2-fluoroethyl, 2,2-dichloro-2-fluoroethyl, 2,2, 2-trichloroethyl and pentafluoroethyl;

$C_1$–$C_4$-haloalkoxy, in particular $C_1$–$C_2$-haloalkoxy such as difluoromethoxy, trifluoromethoxy, chlorodifluorome. 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially trifluoromethoxy;

$C_1$–$C_4$-alkoxy such as methoxy, ethoxy, propoxy, 1-methylethoxy, butoxy, 1-methylpropoxy, 2-methylpropoxy, 1,1-dimethylethoxy, especially methoxy, ethoxy, 1-methylethoxy;

$C_1$–$C_4$-alkylthio such as methylthio, ethylthio, propylthio, 1-methylethylthio, butylthio, 1-methylpropylthio, 2methylpropythio, 1,1-dimethylethylthio, especially methylthio and ethylthio;

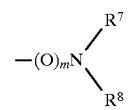

where m is 0 or 1 and R[7] and R[8], which can be identical or different, have the following meanings:
hydrogen
$C_1$–$C_8$-alkyl, especially $C_1$–$C_4$-alkyl as mentioned above;
$C_3$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, especially 2-propenyl, 2-butenyl, 3-methyl-2-butenyl and 3-methyl-2-pentenyl;

$C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl and 1-methyl-2-butynyl, especially 2-propynyl $C_3$–$C_8$-cycloalkyl, such as cyclopropyl, cyclobutyl, cyclo-pentyl, cyclohexyl, cycloheptyl and cyclooctyl, it being possible for these alkyl, cycloalkyl, alkenyl and alkynyl groups in each case to carry from one to five halogen atoms, especially fluorine or chlorine, and/or one or two of the following groups:

$C_1$–$C_4$-alkyl, $C_1$–$C_4$-alkoxy, $C_1$–$C_4$-alkylthio, $C_1$–$C_4$-haloalkoxy as mentioned above, $C_3$–$C_6$-alkenyloxy, $C_3$–$C_6$-alkenylthio, $C_3$–$C_6$-alkynyloxy, $C_3$–$C_6$-alkynylthio, where the alkenyl and alkynyl moieties present in these radicals preferably have the abovementioned meanings;

$C_1$–$C_4$-alkylcarbonyl such as, in particular, methylcarbonyl, ethylcarbonyl, propylcarbonyl, 1-methylethylcarbonyl, butyl-carbonyl, 1-methylpropylcarbonyl, 2-methylpropylcarbonyl, 1,1-dimethylethylcarbonyl;

$C_1$–$C_4$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1methylethoxycarbonyl;

$C_3$–$C_6$-alkenylcarbonyl, $C_3$–$C_6$-alkynylcarbonyl, $C_3$–$C_6$-alkenyloxy-carbonyl, and $C_3$–$C_6$-alkynyloxycarbonyl, where the alkenyl and alkynyl radicals are preferably defined as detailed above;

phenyl which is unsubstituted or substituted one or more times, e.g. from once to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, such as 2-fluorophenyl, 3-chlorophenyl, 4-bromphenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl phenyl, 2-methoxy-3-methylphenyl, 2,4-dimethoxyphenyl, 2-nitro-5-cyanophenyl, 2,6-difluorophenyl;

di-$C_1$–$C_4$-alkylamino such as, in particular, dimethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

$R^7$ and $R^8$ are also phenyl which can be substituted by one or more, e.g. from one to three, of the following radicals: halogen, nitro, cyano, $C_1$–$C_4$-alkyl, $C_1C_4$-haloalkyl, $C_1$–$C_4$-haloalkoxy or $C_1$–$C_4$-alkylthio as mentioned above in particular;

or $R^7$ and $R^8$ together form a $C_4$–$C_7$-alkylene chain which is closed to form a ring and is unsubstituted or substituted, e.g. by $C_1$–$C_4$-alkyl, and can contain a hetero atom selected from the group comprising oxygen, sulfur or nitrogen, such as —(CH$_2$)$_4$—, —(CH$_2$)$_5$—, —(CH$_2$)$_6$—, —(CH$_2$)$_7$—, —(CH$_2$)$_2$(CH$_2$)$_2$—, CH$_2$—S-(CH$_2$)$_3$—, —(CH$_2$)$_2$—(CH$_2$)$_3$—, —NH—(CH$_2$)$_3$—, —CH$_2$—NH—(CH$_2$)$_2$—CH$_2$—CH=CH—CH$_2$—, H=CH—(CH$_2$)3—;

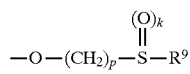

where k is 0, 1 or 2, p is 1, 2, 3 or 4, and $R^9$ is $C_1$–$C_4$-alkyl, $C_1$–$C_4$-haloalkyl, $C_{3-6}$-alkenyl, $C_3$–$C_6$-alkynyl or unsubstituted or substituted phenyl as mentioned above in particular.

f) $R^1$ is also $OR^{10}$ where $R^{10}$ is:

hydrogen, the cation of an alkali metal such as lithium, sodium, potassium or the cation of an alkaline earth metal such as calcium, magnesium and barium or an environmentally compatible organic ammonium ion such as tertiary $C_1$–$C_4$-alkylammonium or the ammonium ion;

$C_3$–$C_9$-Cycloalkyl as mentioned above, which can carry from one to three $C_3$–$C_{14}$-alkyl groups;

$C_1$–$C_8$-alkyl such as, in particular, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, which can carry from one to five halogen atoms, in particular fluorine and chlorine, and/or one of the following radicals:

$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, phenoxy or phenylcarbonyl, where the aromatic radicals can in turn each carry from one to five halogen atoms and/or from one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$-$C_4$-alkylthio, in particular as mentioned above;

$C_1$–$C_8$-alkyl as mentioned above, which can carry from one to five halogen atoms, in particular fluorine and/or chlorine, and carries one of the following radicals: a 5-membered heteroaromatic ring containing from one to three nitrogen atoms, or a 5-membered heteroaromatic ring containing one nitrogen atom and one oxygen or sulfur atom, which can carry from one-to four halogen atoms and/or one or two of the following radicals:

nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. The following may be particularly mentioned: 1-pyrazolyl, 3-methyl-1-pyrazoly, 4-methyl-1-pyrazolyl, 3,5-dimethyl-1-pyrazolyl, 3-phenyl-1-pyrazolyl, 4-phenyl-1-pyrazolyl, 4-chloro-1pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benztriazolyl, 3-isopropyl-5-isoxazolyl, 3-methyl-5-isoxazolyl, 2-thiazolyl, 2-imidazolyl, 3-ethyl-5-isoxazolyl, 3-phenyl-5-isoxazolyl, 3-tert-butyl-5-isoxazolyl;

$C_2$–$C_6$-alkyl which carries one of the following radicals in position 2: $C_1$–$C_4$-alkoxyimino, $C_3$–$C_6$-alkynyloxyimino, $C_3$–$C_6$-haloalkenyloxyimino or benzyloxyimino; $C_{3-6}$-alkenyl or $C_{3-6}$-alkynyl, where these groups in turn can carry from one to five halogen atoms;

$R^{10}$ is also a phenyl which can carry from one to five halogen atoms and/or from one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$-$C_4$-alkylthio, in particular as mentioned above;

a 5-membered heteroaromatic ring which is linked via a nitrogen atom, contains from one to three nitrogen atoms and can carry one or two halogen atoms and/or one or two of the following radicals: $C_1$–$C_4$-alkyl, $C_1$–$C_4$-haloalkyl, $C_1$–$C_4$-alkoxy, phenyl, $C_{14}$-haloalkoxy and/or $C_1$–$C_4$-alkylthio. The following may be particularly mentioned: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1pyrazolyl, 4-bromo-1-pyrazolyl, 1-imidazolyl, 1-benzimidazo lyl, 1,2,4-triazol-1-yl, 3-methyl-1,2,4-triazol-1-yl, 5-methyl-1,2,4-triazol-1-yl, 1-benztriazolyl, 3,4-dichloro-1-imidazolyl;

$R^{10}$ is also a group

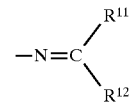

where $R^{11}$ and $R^{12}$, which can be identical or different, are:

$C_1$–$C_9$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio and/or a substituted or unsubstituted phenyl radical, in particular as mentioned above;

phenyl, which can be substituted by one or more, e.g. from one to three, of the following radicals: halogen, nitro, cyano, $C_{1-4}$-alkyl, $C_1$–$C_4$-haloalkyl, $C_1$–$C_4$-alkoxy, $C_1$–$C_4$-haloalkoxy or $C_1$–$C_4$-alkylthio, where these radicals correspond in particular to those mentioned above;

or $R^{11}$ and $R^{12}$ together form a $C_3$–$C_{12}$-alkylene chain which can carry from one to three $C_1$–$C_4$-alkyl groups and contain a hetero atom from the group comprising oxygen, sulfur and nitrogen, in particular as mentioned for $R^7$ and $R^8$.

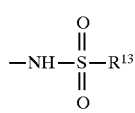

where $R^{13}$ is:

$C_1$–$C_4$-alkyl, $C_3$–$C_6$-alkenyl, $C_{3-6}$-alkynyl, $C_3$–$C_8$-cycloalkyl, in particular as mentioned above, it being possible for these radicals to carry a $C_1$–$C_4$-alkoxy, $C_1$–$C_4$-alkylthio and/or a phenyl radical as mentioned above;

phenyl which is unsubstituted or substituted, in particular as mentioned above.

With a view to the biological effect, preferred carboxylic acid derivatives of the general formula I are those in which the substituents have the following meanings:

$R^2$ the $C_1$–$C_4$-alkyl, $C_{1.4}$-haloalkyl, $C_1$–$C_4$-alkoxy, $C_1$–$C_4$-halogen alkoxy, $C_1$–$C_4$-alkylthio groups and halogen atoms mentioned specifically for $R^1$, in particular chlorine, methyl, methoxy, ethoxy, difluoromethoxy, trifluoromethoxy, particularly preferably methoxy;

X nitrogen or $CR^{14}$ where $R^{14}$ is hydrogen or forms together with $R^3$ a 4- or 5-membered alkylene or alkenylene chain in which, in each case, one methylene group is replaced by oxygen, such as —$CH_2$—$CH_2$—O—, —CH=CH—, $H_2$—$CH_2$—$CH_2$—O—, —CH=CH–$CH_2$0—, in particular hydrogen and —$CH_2$—$CH_2$—O—;

$R^3$ the $C_1$–$C_4$-alkyl, $C_1$–$C_4$-haloalkyl, $C_1$–$C_4$-alkoxy, $C_{1-4}$-haloalkoxy $C_1$–$C_4$-alkylthio groups and halogen atoms mentioned for $R^1$, in particular chlorine, methyl, methoxy, ethoxy, difluoromethoxy, trifluoromethoxy or is linked to $R^{14}$ as mentioned above to form a 5- or 6-membered ring, $R^3$ is particularly preferably methoxy;

$R^4$–$C_1$–Clo-alkyl as specifically mentioned for $R^1$, which can carry from one to five halogen atoms such as fluorine, chlorine, bromine, iodine, in particular fluorine and chlorine, and/or one of the following radicals: alkoxy, alkylthio, cyano, alkylcarbonyl, alkoxycarbonyl, phenyl, phenoxy, phenyl-carbonyl as mentioned in general and in particular for $R^1$;

$C_1$–$C_{10}$-alkyl as mentioned above, which can carry from one to five halogen atoms as mentioned above, in particular fluorine and chlorine, and carries a 5-membered heteroaromatic ring which is unsubstituted or substituted, as mentioned above for $R^1$;

$C_3$ $_{-2}$-cycloalkyl, in particular $C_3$–$C_7$-cycloalkyl, or $C_3$–C12-cycloalkenyl, in particular $C_4$–$C_7$-Cycloalkenyl, it being possible for one methylene group in the saturated or unsaturated ring to be replaced by an oxygen or sulfur atom, such as cyclopropyl, cyclobutyl, cyclopentyl, cyclohexyl, cycloheptyl, tetrahydrofuranyl, tetrahydrothienyl, tetrahydropyranyl, tetrahydrothiopyranyl, cyclopropenyl, dihydrofuranyl, dihydrothienyl, dihydropyranyl, dihydrothiopyranyl, where the cycloalkyl and cycloalkenyl radicals can be substituted by from one to five halogen atoms as mentioned above, especially fluorine or chlorine, and/or one of the following radicals: $C_1$–$C_4$-alkyl, $C_1C_4C_4$-alkoxy, $C_1$ $_4$-alkylthio, cyano, $C_1$–$C_8$-alkylcarbonyl, $C_1$–$C_8$-alkoxycarbonyl, phenyl, phenoxy, phenylcarbonyl as mentioned above in general and in particular;

$C_3$–$C_6$-alkenyl or $C_3$–$C_6$-alkynyl as mentioned for $R^1$, which can carry from one to five halogen atoms as mentioned above, in particular fluorine and chlorine, and/or one of the following radicals:

$C_1$–$C_4$alkyl, $C_1$–$C_4$-alkoxy, $C_1$–$C_4$-alkylthio, cyano, $C_1$–$C_8$-alkyl-carbonyl, $C_1$–(8-akloxycarbonyl, phenyl, phenoxy, phenylcarbonyl as mentioned above in general and in particular;

5- or 6-membered hetaryl such as furyl, thienyl, pyrryl, pyrazolyl, imidazolyl, triazolyl, isoxazolyl, oxazolyl, isothiazolyl, thiazolyl, thiadiazolyl, pyridyl, pyrimidinyl, pyrazinyl, pyridazinyl, triazinyl, for example 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl, 4-pyridyl, oxa-2,4-diazolyl [sic], oxa-3,4-diazoylyl [sic], thia-2,4-diazolyl [sic], thia-3,4-diazolyl [sic] and triazolyl, where the heteroaromatic rings can carry from one to five halogen atoms as mentioned above, in particular fluorine and chlorine, and/or from one to three of the following radicals;

$C_1$–$C_4$-alkyl, $C_1$–$C_4$-alkoxy, $C_1$–$C_4$-alkylthio, cyano, nitro, $C_1$–C-alkylcarbonyl, $C_1$–$C_8$-alkoxycarbonyl, phenyl, phenoxy, phenylcarbonyl as mentioned above in general and in particular;

$R^4$ is also phenyl or naphthyl which can be substituted by one or more, e.g. from one to three, of the following radicals: halogen, nitro, cyano, hydroxyl, mercapto, amino, $C_1C_4$-alkyl, $C_1$–$C_4$-haloalkyl, $C_1$–$C_4$-alkoxy, $C_1$–$C_4$-haloalkoxy, $C_i$–$C_4$-alkyl- thio, $C_1$–$C_4$-alkylamino, di-$C_1$–$C_4$-alkylamino, $C_1$–$C_4$-alkyl-carbonyl, $C_1$–$C_4$-alkoxycarbonyl, in particular as mentioned for $R^7$ and $R^8$, and, for example, 3-hydroxyphenyl, 4-dimethylaminophenyl, 2-mercaptophenyl, 3-methoxycarbonylphenyl, 4-acetyl-1-naphthyl, 2-naphthyl, 3-bromo-2-naphthyl, 4-methyl-1-naphthyl, 5-methoxy-1-naphthyl, 6-trifluoromethyl-1-naphthyl, 7-chlor-1-naphthyl, 8-hydroxy-1-naphthyl; or $R^4$ and $R^5$ form together with the adjacent carbon atom a 3-to 6-membered ring which can contain an oxygen or sulfur atom and is unsubstituted or carries from one to three, depending on the ring size, of the following radicals:

$C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio as mentioned above in general and in particular;

hydrogen, $C_1$–$C_4$-alkyl, $C_3$–$C_6$-alkenyl, $C_3$–$C_6$-alkynyl, $C_3$–$C_8$-cycloalkyl, $C_1$–$C_4$-haloalkyl, $ClC_4$-alkoxyalkyl, $C_1$–$C_4$-alkylthioalkyl or phenyl as mentioned above for $R^4$ in particular;

$R^6$ $C_1$–$C_8$-alkyl, $C_3$–$C_6$-alkenyl, $C_3$–$C_6$-alkynyl or $C_{3-8}$-cycloalkyl as mentioned above in particular, it being possible for each of these radicals to be substituted one or more times by: halogen, nitro, cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, $C_{1-4}$-alkylamino, di-$C_1$–$C_4$-alkylamino or unsubstituted or substituted phenyl or phenoxy as mentioned above in particular;

phenyl or naphthyl which can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1C_4$-akylamino [sic] or $C_1$–$C_4$-dialkylamino as mentioned in particular for $R^7$ and $R^4$;

a five- or six-membered heteroaromatic ring which contains from one to three nitrogen atoms and/or one sulfur or oxygen atom and which can carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio as mentioned in particular for $R^4$;

Y sulfur, oxygen or a single bond

Z sulfur or oxygen.

Particularly preferred compounds of the formula I are those where $R^2$ and $R^3$ are methoxy and X is CH. Also preferred are compounds of the formula I where $R^2$ and $R^3$ are methoxy, X is CH, Y and Z are oxygen and $R^5$ is $C_1$–$C_4$-alkyl. The preferred radical in the case of $R^1$ is $OR^{10}$ where $R^{10}$ is hydrogen or $C_1$-$C_4$-alkyl.

$R^4$ is particularly preferably $C_1$–$C_4$-alkyl, unsubstituted or substituted phenyl or an aromatic heterocyclic radical containing one hetero atom, such as furyl or thienyl.

$R^6$ is particularly preferably phenyl which is unsubstituted or substituted 1-3 times by halogen, $C_1$–$C_4$-alkyl, $C_1$–$C_4$-alkoxy and/or $C_1$–$C_4$-alkylthio.

Examples of preferred compounds are listed in the following Table.

Compounds 4.42 and 4.58 (Example 10, Tab. 4) are particularly preferably used according to the invention.

TABLE

| $R^1$ | $R^4$ | $R^5$ | $R^6$ | $R^2$ | $R^3$ | X | Y | Z |
|---|---|---|---|---|---|---|---|---|
| OH | Phenyl | Methyl | Methyl | $OCH_3$ | $OCH_3$ | CH | S | S |
| OH | Phenyl | Methyl | Methyl | $OCH_3$ | $OCH_3$ | CH | O | S |
| $OCH_3$ | Phenyl | Methyl | Methyl | $OCH_3$ | $OCH_3$ | CH | S | S |
| OH | Phenyl | i-Propyl | Methyl | $OCH_3$ | $OCH_3$ | CH | O | O |
| $OCH_3$ | 2-Fluorophenyl | Ethyl | Methyl | $OCH_3$ | $OCH_3$ | CH | O | O |
| $OC_2H_5$ | 3-Chlorophenyl | Propyl | Methyl | $OCH_3$ | $OCH_3$ | N | O | O |
| $ON(CH_3)_2$ | 4-Bromophenyl | i-Propyl | Methyl | $CF_3$ | $CF_3$ | CH | S | O |
| $ON=C(CH_3)_2$ | 2-Thienyl | Methyl | Methyl | $OCF_3$ | $OCF_3$ | CH | O | S |
| $HNSO_2C_6H_5$ | 3-Thienyl | Methyl | Methyl | $CH_3$ | $CH_3$ | CH | O | O |
| NHPhenyl | 2-Furyl | Methyl | Methyl | Cl | Cl | CH | O | O |
| ONa | 3-Furyl | Methyl | Methyl | $OCH_3$ | —$OCH_2$—$CH_2$— | | S | O |
| O—$CH_2$—C≡CH | Phenyl | Ethyl | Ethyl | $OCH_3$ | $CF_3$ | CH | O | O |
| OH | Phenyl | Propyl | Propyl | $OCH_3$ | $OCF_3$ | CH | O | S |
| $OCH_3$ | Phenyl | i-Propyl | i-Propyl | $OCH_3$ | $CH_3$ | CH | O | O |
| $OC_2H_5$ | Phenyl | Methyl | s-Butyl | $OCH_3$ | Cl | CH | S | O |
| $ON(CH_3)_2$ | 2-Methylphenyl | Methyl | Methyl | $OCH_3$ | $OCH_3$ | CH | O | O |
| $ON(CH_3)_2$ | 3-Methoxyphenyl | Methyl | Methyl | $OCH_3$ | $OCH_3$ | CH | O | O |
| $ON=C(CH_3)_2$ | 4-Nitrophenyl | Methyl | Methyl | $OCH_3$ | $OCH_3$ | CH | O | O |
| NHphenyl | 2-Oxazolyl | Methyl | Methyl | $CF_3$ | $CF_3$ | N | S | O |
| ONa | 4-Oxazolyl | Methyl | 3-Propenyl [sic] | $OCF_3$ | $OCF_3$ | N | O | S |
| O—$CH_2$—C≡CH | 5-Oxazolyl | Methyl | 3-Propynyl [sic] | $CH_3$ | $CH_3$ | N | O | O |
| OH | 3-Isoxazoyl | Methyl | Cyclopentyl | Cl | Cl | N | O | O |
| $OCH_3$ | 4-Isoxazoyl | Methyl | Cyclohexyl | $OCH_3$ | —O—$CH_2$—$CH_2$— | O | O | |
| $OC_2H_5$ | 5-Isoxazoyl | Methyl | Cyclopropylmethyl | $OCH_3$ | $CF_3$ | N | S | O |
| $ON(CH_3)_2$ | Phenyl | Methyl | 1-Phenyl-3-propynyl [sic] | $OCH_3$ | $OCF_3$ | N | O | S |
| $ON=C(CH_3)_2$ | 2-Hydroxyphenyl | Methyl | Methyl | $OCH_3$ | $CH_3$ | N | O | O |
| $ONSO_2C_6H_5$ | 3-Trifluoromethylphenyl | Methyl | Methyl | $OCH_3$ | Cl | N | O | O |
| NHPhenyl | 4-Dimethylaminophenyl | Methyl | Methyl | $OCH_3$ | $OCH_3$ | CH | S | O |
| ONa | 2-Imidazolyl | Ethyl | Methyl | $OCH_3$ | $OCH_3$ | CH | S | S |
| O—$CH_2$—C≡CH | 4-Imidazolyl | Propyl | Methyl | $OCH_3$ | $OCH_3$ | N | S | S |
| OH | 3-Pyrazolyl | i-Propyl | Methyl | $CF_3$ | $CF_3$ | CH | O | S |
| $OCH_3$ | 4-Pyrazolyl | Methyl | Methyl | $OCF_3$ | $OCF_3$ | CH | O | O |
| $OC_2H_5$ | Phenyl | Methyl | Trifluoroethyl | $CH_3$ | $CH_3$ | CH | O | O |
| $ON(CH_3)_2$ | Phenyl | Methyl | Benzyl | Cl | Cl | CH | O | O |
| $ON(CH_3)_2$ | Phenyl | Methyl | 2-Methoxyethyl | $OCH_3$ | —O—$CH_2$—$CH_2$— | | S | O |
| $ON=C(CH_3)_2$ | Phenylpropyl | Methyl | 3-Methoxycarbonyl- [sic] | $OCH_3$ | $CF_3$ | N | S | S |
| NH-Phenyl | 2-Pyridyl | Methyl | 2-Chloroethyl | $OCH_3$ | $OCF_3$ | N | S | S |
| ONa | 3-Pyridyl | Methyl | Methyl | $OCH_3$ | $CH_3$ | N | O | O |
| O—$CH_2$—C≡CH | 4-Pyridyl | Methyl | Methyl | $OCH_3$ | Cl | N | O | O |
| $OCH_3$ | Phenyl | $CH_3$ | Phenyl | $OCH_3$ | $OCH_3$ | CH | O | O |
| OH | Phenyl | $CH_3$ | Phenyl | $OCH_3$ | $OCH_3$ | CH | O | O |
| OH | Phenyl | $CH_3$ | Phenyl | $OCH_3$ | —O—$CH_2$—$CH_2$— | O | O | |
| OH | Phenyl | $CH_3$ | Phenyl | $OCH_3$ | $OCH_3$ | N | O | O |
| OH | Phenyl | $CH_3$ | Phenyl | $OCH_3$ | $OCH_3$ | CH | S | O |
| OH | Phenyl | $CH_3$ | Phenyl | $OCH_3$ | $OCH_3$ | CH | S | S |
| OH | Phenyl | $CH_3$ | Phenyl | $OCH_3$ | $OCH_3$ | CH | O | S |
| OH | Phenyl | H | Phenyl | $OCH_3$ | $OCH_3$ | CH | O | O |
| OH | Phenyl | i-Propyl | Phenyl | $OCH_3$ | $OCH_3$ | CH | O | O |
| OH | $CH_3$ | $CH_3$ | Phenyl | $OCH_3$ | $OCH_3$ | CH | O | O |
| OH | —$(CH_2)_5$— | | Phenyl | Phenyl | $OCH_3$ | CH | O | O |
| OH | Phenyl | $CH_3$ | 2-Thiazolyl | $OCH_3$ | $OCH_3$ | CH | O | O |
| OH | 2-Thienyl | $CH_3$ | Phenyl | $OCH_3$ | $OCH_3$ | CH | O | O |
| $OCH_3$ | 2-Fluorophenyl | Ethyl | Phenyl | $OCH_3$ | $OCH_3$ | CH | O | O |
| $OC_2H_5$ | 3-Chlorophenyl | Propyl | Phenyl | $OCH_3$ | $OCH_3$ | N | O | O |
| $ON(CH_3)_2$ | 4-Bromophenyl | i-Propyl | Phenyl | $CF_3$ | $CF_3$ | CH | S | O |
| $ON=C(CH_3)_2$ | 2-Thienyl | Methyl | Phenyl | $OCF_3$ | $OCF_3$ | CH | O | S |
| NH—$SO_2$—$C_6H_5$ | 3-Thienyl | Methyl | Phenyl | $CH_3$ | $CH_3$ | CH | O | O |
| NHPhenyl | 2-Furyl | Methyl | Phenyl | Cl | Cl | CH | O | O |

TABLE-continued

| R¹ | R⁴ | R⁵ | R⁶ | R² | R³ | X | Y | Z |
|---|---|---|---|---|---|---|---|---|
| ONa | 3-Furyl | Methyl | Phenyl | OCH₃ | —O—CH₂—CH₂— | S | | O |
| O—CH₂≡CH | Phenyl | Ethyl | 2-Fluorophenyl | OCH₃ | CF₃ | CH | O | O |
| OH | Phenyl | Propyl | 3-Chlorophenyl | OCH₃ | OCF₃ | CH | O | S |
| OCH₃ | Phenyl | i-Propyl | 4-Bromophenyl | OCH₃ | CH₃ | CH | O | O |
| OC₂H₅ | Phenyl | Methyl | 4-Thiazolyl | OCH₃ | Cl | CH | S | O |
| ON(CH₃)₂ | 2-Methylphenyl | Methyl | Phenyl | OCH₃ | OCH₃ | CH | O | O |
| ON=C(CH₃)₂ | 3-Methoxyphenyl | Methyl | Phenyl | OCH₃ | OCH₃ | CH | O | O |
| NH—SO—C₆H₅ | 4-Nitrophenyl | Methyl | Phenyl | OCH₃ | OCH₃ | CH | O | O |
| NHPhenyl | Methyl | Methyl | Phenyl | CF₃ | CF₃ | N | S | O |
| ONa | Methyl | Methyl | 2-Methylphenyl | OCF₃ | OCF₃ | N | O | S |
| O—CH₂—C≡CH | Methyl | Methyl | 3-Methoxyphenyl | CH₃ | CH₃ | N | O | O |
| OH | Methyl | Methyl | 4-Nitrophenyl | Cl | Cl | N | O | O |
| OCH₃ | Phenyl | Methyl | 3-Imidazolyl | OCH₃ | —O—CH₂—CH₂— | O | | O |
| OC₂H₅ | Phenyl | Methyl | 4-Imidazolyl | OCH₃ | CF₃ | N | S | O |
| ON(CH₃)₂ | Phenyl | Methyl | 2-Pyrazolyl | OCH₃ | OCF₃ | N | O | S |
| ON=C(CH₃)₂ | 2-Hydroxyphenyl | Methyl | Phenyl | OCH₃ | CH₃ | N | O | O |
| NH—SO₂—C₆H₅ | 3-Trifluoromethylphenyl | Methyl | Phenyl | OCH₃ | Cl | N | O | O |
| NHPhenyl | 4-Dimethylaminophenyl | Methyl | Phenyl | OCH₃ | OCH₃ | CH | S | O |
| ONa | 3-Imidazolyl | Ethyl | Phenyl | OCH₃ | OCH₃ | CH | S | S |
| O—CH₂—C≡CH | 4-Imidazolyl | Propyl | Phenyl | OCH₃ | OCH₃ | N | S | S |
| OH | 3-Pyrazolyl | i-Propyl | Phenyl | CF₃ | CF₃ | CH | O | O |
| OCH₃ | 4-Pyrazolyl | Methyl | Phenyl | OCF₃ | OCF₃ | CH | O | O |
| OC₂H₅ | Phenyl | Methyl | 2-Dimethylaminophenyl | CH₃ | CH₃ | CH | O | O |
| ON(CH₃)₂ | Phenyl | Methyl | 3-Hydroxyphenyl | Cl | Cl | CH | O | O |
| ON=C(CH₃)₂ | Phenyl | Methyl | 4-Trifluoromethyl-phenyl | OCH₃ | —O—CH₂—CH₂— | S | | O |
| NH—SO₂—C₆H₅ | Phenyl | Methyl | 2-Oxazolyl | OCH₃ | CF₃ | N | S | S |
| NH-Phenyl | 2-Pyridyl | Methyl | 4-Isoxazoyl | OCH₃ | OCF₃ | N | S | S |
| ONa | 3-Pyridyl | Methyl | Phenyl | OCH₃ | CH₃ | N | O | O |
| O—CH₂—C≡CH | 4-Pyridyl | Methyl | Phenyl | OCH₃ | Cl | N | O | O |

The compounds of the present invention provide a novel therapeutic potential for the treatment of hypertension, pulmonary hypertension, myocardial infarct, angina pectoris, acute kidney failure, renal insufficiency, cerebral vasospasms, cerebral ischemia, subarachnoid hemorrhage, migraine, asthma, atherosclerosis, endotoxic shock, endotoxin-induced organ failure, intravascular coagulation, restenosis after angioplasty and cyclosporin-induced kidney failure or hypertension.

The good effect of the compounds can be shown in the following experiments:

Receptor-binding studies

Cloned human ETA receptor-expressing CHO cells and guinea pig cerebellar membranes with>60% ETB receptors compared with ETA receptors were used for binding studies.

Membrane preparation

The ETA receptor-expressing CHO cells were grown in $F_{12}$ medium with 10% fetal calf serum, 1% glutamine, 100 U/ml penicillin and 0.2% streptomycin (Gibco BRL, Gaithersburg, Md., USA). After 48 h, the cells were washed with PBS and incubated with 0.05% trypsin-containing PBS for 5 min. The mixture was then neutralized with $F_{12}$ medium and the cells were collected by centrifugation at 300 xg. For lysis of the cells, the pellet was briefly washed with lysis buffer (5 mM tris-HCl, pH 7.4 with 10% glycerol) and then incubated at a concentration of $10^7$ cells/ml of lysis buffer at 4° C. for 30 min. The membranes were centrifuged at 20,000xg for 10 min, and the pellet was stored in liquid nitrogen.

Guinea pig cerebella were homogenized in a Potter-Elvejhem homogenizer and obtained by differential centrifugation at 1000xg for 10 min and repeated centrifugation of the supernatant at 20,000xg for 10 min.

Binding assays

For the ETA and ETB receptor binding assay, the membranes were suspended in incubation buffer (50 mM tris-HCl, pH 7.4 with 5 mM $MnCl_2$, 40 μg/ml bacitracin and 0.2% BSA) at a concentration of 50 μg of protein per assay mixture and incubated at 25° C. with 25 pM [125I]-$ET_1$ [sic] ($ET_A$ receptor assay) or 25 pM [125I]-$RZ_3$ [sic] (ETB receptor assay) in the presence and absence of test substance. The non-specific binding was determined using $10^{-7}$ M $ET_1$. After 30 min, the free and the bound radioligand were separated by filtration through a GF/B glass fiber filter (Whatman, England) in a Skatron cell collector (Skatron, Lier, Norway), and the filters were washed with ice-cold tris-HCl buffer, pH 7.4 with 0.2% BSA. The radioactivity collected on the filters was quantified using a Packard 2200 CA liquid scintillation counter.

The $K_i$ values were determined by non-linear regression analysis using the LIGAND program.

Table A shows the effect of compounds of the formula I as the $K_i$ [mol/l] determined in the experiments.

TABLE A

| | $K_i$ [mol/l] | |
|---|---|---|
| Compound | ET-A | ET-B |
| 4.42 | 2.5 × 10⁻⁷ | 3.0 × 10⁻⁶ |
| 4.58 | 1.6 × 10⁻⁷ | 4.7 × 10⁻⁶ |

Functional in vitro assay system for searching for endothelin receptor (subtype A) antagonists This assay system is a functional cell-based assay for endothelin receptors. Certain cells when stimulated with endothelin 1 (ET1) show an increase in the intracellular calcium concentration. This increase can be measured in intact cells which have been loaded with calcium-sensitive dyes.

1-Fibroblasts which have been isolated from rats and in which an 35 endogenous endothelin receptor of subtype A has been detected were loaded with the fluorescent dye Fura 2-an as follows: after trypsinization the cells were resuspended in buffer A (120 mM NaCl, 5 mM KCl, 1.5 mM MgCl$_2$, 1 mM CaCl$_2$, 25 mM HEPES, 10 mM glucose, pH 7.4) to a density of 2 x 10$^6$/ml and incubated with Fura 2-am (2 μM), Pluronics F-127 (0.04%) and DMSO (0.2%) at 37° C. in the dark for 30 min. The cells were then washed twice with buffer A and resuspended at 2 10$^6$/ml.

The fluorescence signal at Ex/Em 380/510 from 2×10$^5$ cells per mL was recorded continuously at 30° C. The test substances were added to the cells and, after incubation with ET1 for 3 min, the maximum change in the fluorescence was determined. The response of the cells to ET1 without previous addition of a test substance served as control and was set equal to 100%.

Table B indicates the effect of the compounds of the formula I as the IC$_{50}$ [mol/l] determined in the experiments.

| Compound | IC$_{50}$ [mol/l] |
|---|---|
| 4.42 | 7.4 × 10$^{-7}$ |
| 4.58 | 1.0 × 10$^{-6}$ |

Testing of ET antagonists in vivo

Male SD rats weighing 250–300 g were anesthetized with amobarbital, artificially ventilated, vagotomized and pithed. The carotid artery and jugular vein were catheterized.

In control animals, intravenous administration of 1 μg/kg ET1 leads to a distinct rise in blood pressure which persists for a lengthy period.

5 min before administration of ET1, the test animals received the test compounds by i.v. injection (1 ml/kg). To determine the ET-antagonistic properties, the rise in blood pressure for the test animals was compared with that for the controls.

Endothelin-1-induced sudden death in mice

The test is based on the inhibition of the sudden heart death of mice which is caused by endothelin, probably by constriction of the coronary vessels, on pretreatment with endothelin receptor antagonists. Intravenous injection of 10 nmol/kg endothelin in a volume of 5 ml/kg of body weight is followed within a few minutes, by the death of the animals.

The lethal endothelin-1 dose is checked in each case on a small group of animals. Intravenous administration of the test substance is followed, usually after 5 min, by the lethal endothelin-1 injection in the reference group. With other modes of administration the times between the doses are longer, where appropriate up to several hours.

The survival rate is recorded and effective doses for protection of 50% of the animals (ED 50) against endothelin-induced heart death for 24 h or longer are determined.

Functional vessel test for endothelin receptor antagonists

Initially, a contraction is induced by K$^+$ in segments of rabbit aorta after an initial tension of 2 g and a relaxation time of 1 h in Krebs-Henseleit solution at 37° C. and pH 7.3–7.4. After washing out, an endothelin dose-response plot is constructed up to a maximum.

Potential endothelin antagonists are administered to other specimens of the same vessel 15 min before starting the endothelin dose-response plot. The effects of the endothelin are calculated as a % of the K$^+$-induced contraction. Effective endothelin antagonists cause a shift to the right in the endothelin dose-response plot.

The compounds according to the invention can be administered orally or parenterally (subcutaneously, intravenously, intramuscularly, intraperitoneally) in a conventional way. Administration can also take place with vapors or sprays through the nasal pharyngeal space.

The dosage depends on the age, condition and weight of the patient and on the mode of administration. As a rule, the daily dose of active substance is about 0.5–50 mg/kg of body weight on oral administration and about 0.1–10 mg/kg of body weight on parenteral administration.

The novel compounds can be administered in conventional solid or liquid pharmaceutical forms, eg. uncoated or (film-)coated tablets, capsules, powders, granules, suppositories, solutions, ointments, creams or sprays. These are produced in a conventional way. For this purpose the active substances can be processed with conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The forms obtained in this way normally contain from 40 0.1 to 90% by weight of active substance.

DESCRIPTION OF THE PREFERRED EMBODIMENTS

Synthesis Examples

Synthesis of compounds of the general formula VI

EXAMPLE 1

Methyl 3-methoxy-3-(3-methoxyphenyl)-2-hydroxybutyrate 19.5 g (88 mmol) of methyl 3-(3-methoxyphenyl)-2,3-epoxybutyrate are dissolved in 200 ml of absolute methanol, and 0.1 ml of boron trifluoride etherate is added. The mixture is stirred at room temperature for 12 hours and the solvent is removed by distillation. The residue is taken up in ethyl acetate, washed with sodium bicarbonate solution and water and dried over sodium sulfate. After removal of the solvent by distillation, 21.1 g of a pale yellow oil remain.

Yield: 94% (1:1 mixture of diastereomers)

EXAMPLE 2

Methyl 3-benzyloxy-3-phenyl-2-hydroxybutyrate 9.6 g (50 mmol) of methyl 3-phenyl-2,3-epoxybutyrate are dissolved in 150 ml of benzyl alcohol, and 0.5 ml of concentrated sulfuric acid is added. The mixture is stirred at 50° C. for 6 hours and allowed to cool to room temperature. After neutralization with sodium bicarbonate solution, the excess benzyl alcohol is removed by distillation under high vacuum, and the residue is purified by flash chromatography on silica gel with 9:1 n-hexane/ethyl acetate. After removal of the solvent by distillation, 6.5 g of a colorless oil remain.

Yield: 43% (3:2 mixture of diastereomers)

All the compounds mentioned in Table 1 were prepared in a similar way.

TABLE 1

Intermediates of the formula VI with $R^1 = CH_3$ $$R^6-O-\underset{\underset{R^5}{|}}{\overset{\overset{R^4}{|}}{C}}-\underset{\underset{COOCH_3}{|}}{\overset{|}{CH}}-OH$$

| No. | $R^6$ | $R^4$ | $R^5$ | DR* | M.p. [° C.] |
|---|---|---|---|---|---|
| 1.1 | Methyl | 3-Methoxyphenyl | Methyl | 1:1 | Oil |
| 1.2 | Benzyl | Phenyl | Methyl | 3:2 | Oil |
| 1.3 | Methyl | 2-Fluorophenyl | Methyl | 1:1 | Oil |
| 1.4 | Methyl | 4-i-Propylphenyl | Methyl | | |
| 1.5 | Methyl | 2-Methylphenyl | Methyl | 2:1 | Oil |
| 1.6 | Methyl | 3-Methylphenyl | Methyl | | |
| 1.7 | Methyl | 4-Methylphenyl | Methyl | 3:2 | Oil |
| 1.8 | Methyl | 3-Nitrophenyl | Methyl | | |
| 1.9 | Methyl | 4-Bromophenyl | Methyl | 3:1 | Oil |
| 1.10 | Methyl | 2-Furyl | Methyl | | |
| 1.11 | Methyl | 3-Furyl | Methyl | | |
| 1.12 | Methyl | 2-Thienyl | Methyl | | |
| 1.13 | Methyl | 3-Thienyl | Methyl | | |
| 1.14 | Methyl | 2-Pyridyl | Methyl | | |
| 1.15 | Methyl | 3-Pyridyl | Methyl | | |
| 1.16 | Methyl | 4-Pyridyl | Methyl | | |
| 1.17 | Methyl | 2-Thiazolyl | Methyl | | |
| 1.18 | Methyl | 3-Isoxazolyl | Methyl | | |
| 1.19 | Methyl | 4-Imidazolyl | Methyl | | |
| 1.20 | Methyl | 2-Pyrazolyl | Methyl | | |
| 1.21 | Methyl | 4-Chlorophenyl | Methyl | 2:1 | Oil |
| 1.22 | Benzyl | 3-Methylphenyl | Methyl | 1:1 | Oil |
| 1.23 | Methyl | 4-Fluorophenyl | Methyl | 1:1 | Oil |
| 1.24 | Benzyl | 4-Bromophenyl | Methyl | 1:1 | Oil |
| 1.25 | Benzyl | 4-Chlorophenyl | Methyl | 3:2 | Oil |
| 1.26 | Benzyl | 4-Fluorophenyl | Methyl | 1:1 | Oil |
| 1.27 | Methyl | Phenyl | Ethyl | 1:1 | Oil |
| 1.28 | Methyl | 3-Nitrophenyl | Methyl | 2:1 | Oil |
| 1.29 | Ethyl | 4-Methylphenyl | Methyl | 1:1 | Oil |
| 1.30 | Benzyl | 4-Methylphenyl | Methyl | 1:1 | Oil |
| 1.31 | Benzyl | Phenyl | Ethyl | 1:0 | Oil |
| 1.32 | 4-Fluorobenzyl | Phenyl | Methyl | 1:1 | Oil |

*Diastereomer ratio

Synthesis of compounds of the general formula I:

EXAMPLE 3

Methyl 3-benzyloxy-3-phenyl-2-(4,6-dimethoxy-2-pyrimidinyl)oxybutyrate [sic]

3 g (10 mmol) of methyl 3-benzyloxy-3-phenyl-2-hydroxybutyrate (comp. 1.1) are dissolved in 40 ml of dimethylformamide, and 0.3 g (12 mmol) of sodium hydride is added. The mixture is stirred for 1 hour and then 2.2 g (10 mmol) of 4,6-dimethoxy-2-methylsulfonylpyrimidine are added. The mixture is stirred at room temperature for 24 hours and then cautiously hydrolyzed with 10 ml of water, the pH is adjusted to 5 with acetic acid, and the solvent is removed by distillation under high vacuum. The residue is taken up in 100 ml of ethyl acetate, washed with water, dried over sodium sulfate and distilled to remove solvents. 10 ml of methyl t-butyl ether are added to the residue, and the precipitate is filtered off with suction. Drying results in 2.4 g of a white powder.

Yield: 55% (1:1 mixture of diastereomers)

M.p.: 115°–117° C.

EXAMPLE 4

3-Benzyloxy-3-phenyl-2-(4,6-dimethoxy-2-pyrimidinyl)oxybutyric [sic] acid 1.4 g (3 mmol) of methyl 3-benzyloxy-3-phenyl-2-(4,6-dimethoxy 2-pyrimidinyl)oxybutyrate [sic] (Example 3) are dissolved in 20 ml of methanol and 20 ml of tetrahydrofuran, and 3.7 g of 10% NaOH solution are added. The mixture is stirred at 60° C. for 6 hours and at room temperature for 12 hours, the solvent is removed by distillation under reduced pressure, and the residue is taken up in 100 ml of water. The mixture is extracted with ethyl acetate to remove unreacted ester. The aqueous phase is then adjusted to pH 1–2 with dilute hydrochloric acid and extracted with ethyl acetate. After drying over magnesium sulfate and removal of the solvent by distillation, a little acetone is added to the residue, and the precipitate is filtered off with suction. Drying results in 1.2 g of a white powder.

Yield: 88% (3:2 mixture of diastereomers)

M.p.: 165° C. (decomposition)

EXAMPLE 5

Methyl 3-benzyloxy-3-phenyl-2-[(4,6-dimethoxy-2-pyrimidinyl) thio]butyrate [sic]

11 g (25 mmol) of methyl 3-benzyloxy-3-phenyl-2-hydroxybutyrate (comp. 1.1) are dissolved in 50 ml of dichloromethane, 3 g (30 mmol) of triethylamine are added and, while stirring, 3.2 g (28 mmol) of methanesulfonyl chloride are added dropwise. The mixture is stirred at room temperature for 2 hours, washed with water, dried over magnesium sulfate and concentrated under reduced pressure. The residue is taken up in DMF and added dropwise to a suspension of 12.9 g (75 mmol) of 4,6-dimethoxypyrimidine-2-thiol and 8.4 g (100 nmol) of sodium DMF at 0° C. After stirring at room temperature for 2 hours and at 60° C. for a further 2 hours, the mixture is poured into 1 l of ice-water, and the precipitate is filtered off with suction. Drying results in 3.2 g of a white powder.

Yield: 29% (1:1 mixture of diastereomers)

The compounds specified in Table 2 were prepared in a similar way to the above examples.

TABLE 2

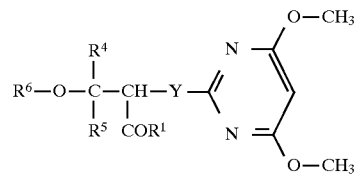

| No. | $R^6$ | $R^4$ | $R^5$ | Y | $R^1$ | Diastereomers | M.p. (°C.) |
|---|---|---|---|---|---|---|---|
| 2.1 | Benzyl | Phenyl | Methyl | O | OCH₃ | 1:1 | 115–117 |
| 2.2 | Benzyl | Phenyl | Methyl | O | OH | 3:2 | 165 (decomp.) |
| 2.3 | Benyzl | Phenyl | Methyl | S | OCH₃ | 1:1 | |
| 2.4 | Benzyl | Phenyl | Methyl | S | OH | | |
| 2.5 | Methyl | 2-Fluorophenyl | Methyl | O | OCH₃ | 1:1 | 126–128 |
| 2.6 | Methyl | 2-Fluorophenyl | Methyl | O | OH | 2:1 | 185–186 |
| 2.7 | Methyl | 3-Methoxyphenyl | Methyl | O | OCH₃ | 1:0 (5:1) | 131–132 (93–95) |
| 2.8 | Methyl | 3-Methoxyphenyl | Methyl | O | OH | 1:0 | 187–189 |
| 2.9 | Methyl | 4-i-Propylphenyl | Methyl | O | OCH₃ | | |
| 2.10 | Methyl | 4-i-Propylphenyl | Methyl | O | OH | | |
| 2.11 | Methyl | 2-Methylphenyl | Methyl | O | OCH₃ | 3:1 | 122–124 |
| 2.12 | Methyl | 2-Methylphenyl | Methyl | O | OH | 1:1 | 135–437 |
| 2.13 | Methyl | 3-Methylphenyl | Methyl | O | OCH₃ | 1:1 | 105–110 |
| 2.14 | Methyl | 3-Methylphenyl | Methyl | O | OH | 1:1 | 130–132 |
| 2.15 | Methyl | 4-Methylphenyl | Methyl | O | OCH₃ | 1:1 | 99–102 |
| 2.16 | Methyl | 4-Methylphenyl | Methyl | O | OH | 1:1 | 145–147 |
| 2.17 | Methyl | 4-Bromophenyl | Methyl | O | OCH₃ | 1:0 | 148–150 |
| 2.18 | Methyl | 4-Bromophenyl | Methyl | O | OH | 1:0 | 189–190 |
| 2.19 | Methyl | 2-Furyl | Methyl | O | OCH₃ | | |
| 2.20 | Methyl | 2-Furyl | Methyl | O | OH | | |
| 2.21 | Methyl | 3-Furyl | Methyl | O | OCH₃ | | |
| 2.22 | Methyl | 3-Furyl | Methyl | O | OH | | |
| 2.23 | Methyl | 2-Thienyl | Methyl | O | OCH₃ | | |
| 2.24 | Methyl | 2-Thienyl | Methyl | O | OH | | |
| 2.25 | Methyl | 2-Pyridyl | Methyl | O | OCH₃ | 2:1 | Oil |
| 2.26 | Methyl | 2-Pyridyl | Methyl | O | ONa | | 175–176 |
| 2.27 | Methyl | 3-Pyridyl | Methyl | O | OCH₃ | | |
| 2.28 | Methyl | 3-Pyridyl | Methyl | O | OH | | |
| 2.29 | Methyl | 4-Pyridyl | Methyl | O | OCH₃ | | |
| 2.30 | Methyl | 4-Pyridyl | Methyl | O | OH | | |
| 2.31 | Methyl | 3-Chlorophenyl | Methyl | O | OCH₃ | | |
| 2.32 | Methyl | 3-Chlorophenyl | Methyl | O | OH | | |
| 2.33 | Methyl | 2-Thiazolyl | Methyl | O | OCH₃ | | |
| 2.34 | Methyl | 2-Thiazolyl | Methyl | O | OH | | |
| 2.35 | Methyl | 3-Isoxazolyl | Methyl | O | OCH₃ | | |
| 2.36 | Methyl | 3-Isoxazolyl | Methyl | O | OH | | |
| 2.37 | Methyl | 4-Imidazolyl | Methyl | O | OCH₃ | | |
| 2.38 | Methyl | 4-Imidazolyl | Methyl | O | OH | | |
| 2.39 | Methyl | 2-Pyrazolyl | Methyl | O | OCH₃ | | |
| 2.40 | Methyl | 2-Pyrazolyl | Methyl | O | OH | | |
| 2.41 | Benzyl | 4-Chlorophenyl | Methyl | O | OCH₃ | 1:1 | 112–114 |
| 2.42 | Benzyl | 4-Chlorophenyl | Methyl | O | OH | | |
| 2.43 | i-Propyl | 2-Fluorophenyl | Methyl | O | OCH₃ | 4:1 | 115–120 |
| 2.44 | i-Propyl | 2-Fluorophenyl | Methyl | O | OH | 2:1 | 143–145 |
| 2.45 | Methyl | 4-Fluorophenyl | Methyl | O | OCH₃ | 1:1 | 122–125 |
| 2.46 | Methyl | 4-Fluorophenyl | Methyl | O | OH | 3:1 | 170–172 |
| 2.47 | Benzyl | 3-Methylphenyl | Methyl | O | OCH₃ | 1:1 | 94–95 |
| 2.48 | Benzyl | 3-Methylphenyl | Methyl | O | OH | 1:1 | 154–156 |
| 2.49 | Methyl | 4-Chlorophenyl | Methyl | O | OCH₃ | 1:1 | 125–127 |
| 2.50 | Methyl | 4-Chlorophenyl | Methyl | O | OH | 5:1 | 206–207 |
| 2.51 | Methyl | Phenyl | Ethyl | O | OCH₃ | 1:0 | 95–100 |
| 2.52 | Methyl | Phenyl | Ethyl | O | OH | 1:0 | 140–142 |
| 2.53 | Benzyl | 4-Fluorophenyl | Methyl | O | OCH₃ | 1:1 | 95–98 |
| 2.54 | Benzyl | 4-Fluorophenyl | Methyl | O | OH | 4:1 | 153–154 |
| 2.55 | 4-Fluoro-benzyl | Phenyl | Methyl | O | OCH₃ | 1:0 | 152–153 |
| 2.56 | 4-Fluoro-benzyl | Phenyl | Methyl | O | OH | 7:3 | 160–162 |
| 2.57 | 4-Bromobenzyl | Phenyl | Methyl | O | OCH₃ | 9:1 | 158–160 |
| 2.58 | 4-Bromobenzyl | Phenyl | Methyl | O | OH | 1:0 | 203–204 |
| 2.59 | Benzyl | 2-Fluorophenyl | Methyl | O | OCH₃ | 1:0 | 129–130 |
| 2.60 | Benzyl | 2-Fluorophenyl | Methyl | O | OH | 1:0 | 200–201 |
| 2.61 | Benzyl | 4-Bromophenyl | Methyl | O | OCH₃ | 1:1 | 78–79 |
| 2.62 | Benzyl | 4-Bromophenyl | Methyl | O | OH | 1:1 | 156–158 |
| 2.63 | Benzyl | 4-Methylphenyl | Methyl | O | OCH₃ | 1:1 | Oil |
| 2.64 | Benzyl | 4-Methylphenyl | Methyl | O | OH | 4:1 | 158–159 |
| 2.65 | Benzyl | Phenyl | Ethyl | O | OCH₃ | 1:0 | 110–112 |
| 2.66 | Benzyl | Phenyl | Ethyl | O | OH | 1:0 | 92–93 |

TABLE 2-continued $$R^6-O-\underset{\underset{R^5}{|}}{\overset{\overset{R^4}{|}}{C}}-\underset{\underset{COR^1}{|}}{CH}-Y-\left\langle\begin{array}{c}N=\\N=\end{array}\right\rangle\begin{array}{c}O-CH_3\\O-CH_3\end{array}$$

| No. | $R^6$ | $R^4$ | $R^5$ | Y | $R^1$ | Diastereomers | M.p. (°C.) |
|---|---|---|---|---|---|---|---|
| 2.67 | Ethyl | 4-Methylphenyl | Methyl | O | OCH₃ | 1:0 | 117–119 |
| 2.68 | Ethyl | 4-Methylphenyl | Methyl | O | OH | 1:1 | Oil |
| 2.69 | Methyl | 2-Furyl | H | O | OCH₃ | 1:1 | Oil |
| 2.70 | Methyl | 2-Furyl | H | O | OH | 1:1 | Oil |
| 2.71 | 4-Chlorobenzyl | Phenyl | Methyl | O | OCH₃ | 1:0 | 172–174 |
| 2.72 | 4-Chlorobenzyl | Phenyl | Methyl | O | OH | 1:0 | 60–61 |
| 2.73 | 2-Butyl | 4-Bromophenyl | Methyl | O | OCH₃ | — | 104–106 |
| 2.74 | 2-Butyl | 4-Bromophenyl | Methyl | O | OH | 1:0 | 153–154 |
| 2.75 | n-Propyl | 4-Fluorophenyl | Methyl | O | OCH₃ | 9:1 | 119–120 |
| 2.76 | n-Propyl | 4-Fluorophenyl | Methyl | O | OH | 9:1 | 104–105 |
| 2.77 | Methyl | 3-Nitrophenyl | Methyl | O | OCH₃ | 1:1 | 101–102 |
| 2.78 | Methyl | 3-Nitrophenyl | Methyl | O | OH | 1:1 | 165–172 |
| 2.79 | Methyl | 4-Trifluorophenyl | Methyl | O | OCH₃ | 1:0 | 112–113 |
| 2.80 | Methyl | 4-Trifluorophenyl | Methyl | O | OH | 4:1 | 68–70 |
| 2.81 | Methyl | 3-Thienyl | H | O | OCH₃ | 1:1 | 80–82 |
| 2.82 | Methyl | 3-Thienyl | H | O | OH | 1:1 | Oil |
| 2.83 | 4-Chlorobenzyl | Phenyl | Methyl | O | OCH₃ | 0:1 | 112–113 |
| 2.84 | 4-Chlorobenzyl | Phenyl | Methyl | O | OCH₃ | 0:1 | 60–61 |
| 2.85 | Methyl | Phenyl | Ethyl | O | OCH₃ | 1:3 | 125–130 |
| 2.86 | Methyl | Phenyl | Ethyl | O | OCH₃ | 0:1 | 133–135 |
| 2.87 | Benzyl | 3-Methoxyphenyl | Methyl | O | OCH₃ | 3:1 | 86–87 |
| 2.88 | Benzyl | 3-Methoxyphenyl | Methyl | O | OH | 1:0 | 155 |
| 2.89 | Benzyl | 3-Methoxyphenyl | Methyl | O | OH | 0:1 | 138–140 |
| 2.90 | 2-Phenylethyl | Phenyl | Methyl | O | OH | 1:0 | 147–149 |
| 2.91 | Methyl | 3-Furyl | H | O | OCH₃ | 1:1 | Oil |
| 2.92 | Methyl | 3-Furyl | H | O | OH | 1:1 | 131–135 |
| 2.93 | 3-CF₃-benzyl | Phenyl | Methyl | O | OCH₃ | 2:1 | 151–152 |
| 2.94 | 3-CF₃-benzyl | Phenyl | Methyl | O | OH | 1:1 | Oil |
| 2.95 | 2-Fluorobenzene [sic] | Phenyl | Methyl | O | OCH₃ | 2:1 | 170–173 |
| 2.96 | 2-Fluorobenzene [sic] | Phenyl | Methyl | O | OH | 1:0 | 160–162 |
| 2.97 | 2-Fluorobenzyl | Phenyl | Methyl | O | OH | 1:3 | 138–141 |
| 2.98 | 3-Fluorobenzyl | Phenyl | Methyl | O | OCH₃ | 1:1 | 81–86 |
| 2.99 | 3-Fluorobenzyl | Phenyl | Methyl | O | OH | 4:1 | 195–197 |
| 2.100 | 3-Fluorobenzyl | Phenyl | Methyl | O | ONa | 3:1 | 250–260 |
| 2.101 | 4-Fluorobenzyl | Phenyl | Methyl | O | OCH₃ | 1:1 | 112–115 |
| 2.102 | 4-Fluorobenzyl | Phenyl | Methyl | O | OH | | |

Synthesis of compounds of the general formula VI:

EXAMPLE 6

Methyl 3-phenoxy-3-phenyl-3-hydroxybutyrate 28.2 g (0.3 mol) of phenol and 19.2 g (0.1 mol) of methyl 3-phenyl-2,3-epoxybutyrate are heated together at 100° C. for 6 hours. Removal of the excess phenol by distillation under high vacuum and purification of the residue by chromatography on silica gel with hexane/ethyl acetate mixtures result in 17.9 g of a pale yellow oil.

Yield: 62.5%

EXAMPLE 7

Methyl 3-(4-bromophenyl)oxy-3-phenyl-2-hydroxybutyrate [sic]

51.9 g (0.3 mol) of 4-bromophenol and 19.2 g (0.1 mol) of methyl 3-phenyl-2,3-epoxybutyrate are stirred at 100° C. for 8 h and at room temperature for 12 h. After removal of the excess phenol by distillation, the residue is purified by flash chromatography (silica gel, n-hexane/ethyl acetate 9:1) to result in 7.2 g of a white solid.

Yield: 20%

M.p.: 133°–135° C.

The compounds specified in Table 3 were prepared in a similar way:

TABLE 3

Intermediates of the formula VI with $R^1 = CH_3$ $$R^6-O-\underset{\underset{COOCH_3}{|}}{\overset{\overset{R^4}{|}}{C}}-\underset{}{CH}-OH$$
$$\phantom{R^6-O-C-}R^5$$

| | $R^6$ | $R^4$ | $R^5$ | M.p. [°C.] |
|---|---|---|---|---|
| 3.1 | Phenyl | Phenyl | Methyl | Oil |
| 3.2 | 4-Bromophenyl | Phenyl | Methyl | 130–133 |
| 3.3 | Phenyl | Methyl | Methyl | |
| 3.4 | Phenyl | Phenyl | i-Propyl | |
| 3.5 | 2-Fluorophenyl | Phenyl | Methyl | |
| 3.6 | 3-Fluorophenyl | Phenyl | Methyl | Oil |
| 3.7 | 4-Fluorophenyl | Phenyl | Methyl | Oil |
| 3.8 | 4-Chlorophenyl | Phenyl | Methyl | |
| 3.9 | 4-Nitrophenyl | Phenyl | Methyl | |
| 3.10 | 4-Methylphenyl | Phenyl | Methyl | Oil |
| 3.11 | Phenyl | 2-Fluorophenyl | Methyl | |
| 3.12 | Phenyl | 3-Methoxyphenyl | Methyl | |
| 3.13 | Phenyl | 4-i-Propylphenyl | Methyl | |
| 3.14 | Phenyl | 2-Methylphenyl | Methyl | |
| 3.15 | Phenyl | 3-Nitrophenyl | Methyl | |
| 3.16 | Phenyl | 4-Bromophenyl | Methyl | |
| 3.17 | Phenyl | 2-Furyl | Methyl | |
| 3.18 | Phenyl | 2-Thienyl | Methyl | Oil |
| 3.19 | Phenyl | 3-Furyl | Methyl | |
| 3.20 | Phenyl | 3-Thienyl | Methyl | |
| 3.21 | 3-Methylphenyl | Phenyl | Methyl | Oil |
| 3.22 | 2-Methylphenyl | Phenyl | Methyl | Oil |
| 3.23 | 4-i-Propylphenyl | Phenyl | Methyl | Oil |
| 3.24 | Phenyl | 4-Chlorophenyl | Methyl | Oil |

Synthesis of compounds of the general formula I:

EXAMPLE 8

Methyl 3-phenoxy-3-phenyl-2-(4,6-dimethoxy-2-pyrimidinyl)oxybutyrate [sic]

4.4 g (15.4 mmol) of methyl 3-phenoxy-3-phenyl-2-hydroxybutyrate (compound 1.1) [sic] are dissolved in 40 ml of dimethylformamide, and 0.46 g (18.4 mmol) of sodium hydride is added. The mixture is stirred for 1 hour and then 3.4 g (15.4 mmol) of 4,6-dimethoxy-2-methylsulfonylpyrimidine are added. The mixture is stirred at room temperature for 24 hours and then cautiously hydrolyzed with 10 ml of water, the pH is adjusted to 5 with acetic acid, and the solvent is removed by distillation under high vacuum. The residue is taken up in 100 ml of ethyl acetate, washed with water, dried over sodium sulfate and distilled to remove solvents. 10 ml of methyl t-butyl ether are added to the residue, and the precipitate is filtered off with suction. Drying results in 1.6 g of a white powder.

Yield: 24.5%

M.p.: 143°–145° C.

EXAMPLE 9

3-Phenoxy-3-phenyl-2-(4,6-dimethoxy-2-pyrimidinyl)oxybutyric [sic] acid 1.3 g of methyl 3-phenoxy-3-phenyl-2-(4,6-dimethoxy-2-pyrimidinyl) oxybutyrate [sic] (Example 8) are dissolved in 20 ml of MeOH and 40 ml of tetrahydrofuran, and 3.7 g of 10% NaOH solution are added. The mixture is stirred at 60° C. for 6 hours and at room temperature for 12 hours, the solvent is removed by distillation under reduced pressure, and the residue is taken up in 100 ml of water. Unreacted ester is extracted with ethyl acetate. The aqueous phase is then adjusted to pH 1–2 with dilute hydrochloric acid and extracted with ethyl acetate. Drying over magnesium sulfate and removal of the solvent by distillation result in 1.0 g of a white powder.

Yield: 79.7%

M.p.: 50°–55° C.

EXAMPLE 10

Methyl 3-phenoxy-3-phenyl-2-[(4,6-dimethoxy-2-pyrimidinyl) thio]butyrate [sic]

7.2 g (25 mmol) of methyl 3-phenoxy-3-phenyl-2-hydroxybutyrate (comp. 1.1) are dissolved in 50 ml of dichloromethane, 3 g (30 mmol) of triethylamine are added and, while stirring, 3.2 g (28 mmol) of methanesulfonyl chloride are added dropwise. The mixture is stirred at room temperature for 2 hours, washed with water, dried over magnesium sulfate and concentrated under reduced pressure. The residue is taken up in 100 ml of DMF and added dropwise to a suspension of 12.9 g (75 mmol) of 4,6-dimethoxypyrimidine-2-thiol and 8.4 g (100 nm mmol) of sodium bicarbonate in 100 ml of DMF at 0° C. After stirring at room temperature for 2 hours and at 60° C. for a further 2 hours, the mixture is poured into 1 1 of ice-water, and the precipitate is filtered off with suction. Drying results in 4.2 g of a white powder.

Yield: 38%

The compounds specified in Table 4 were prepared in a similar way to the above examples.

TABLE 4

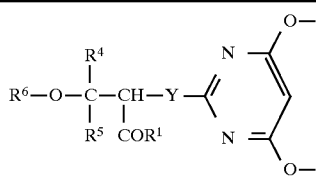

| Ex. No. | $R^6$ | $R^4$ | $R^5$ | $R^1$ | Y | M.p. [°C.] |
|---|---|---|---|---|---|---|
| 4.1 | Phenyl | Phenyl | Methyl | $OCH_3$ | O | 100–103 |
| 4.2 | Phenyl | Phenyl | Methyl | OH | O | 50–55 |
| 4.3 | Phenyl | Phenyl | Methyl | $OCH_3$ | S | |
| 4.4 | Phenyl | Phenyl | Methyl | OH | S | |
| 4.5 | Phenyl | Phenyl | i-Propyl | $OCH_3$ | O | |

TABLE 4-continued $$R^6-O-\underset{\underset{COR^1}{|}}{\overset{\overset{R^4}{|}}{C}}-CH-Y-\text{[pyrimidine with 2 O substituents]}$$

| Ex. No. | $R^6$ | $R^4$ | $R^5$ | $R^1$ | Y | M.p. [°C.] |
|---|---|---|---|---|---|---|
| 4.6 | Phenyl | Phenyl | i-Propyl | OH | O | |
| 4.7 | Phenyl | Methyl | Methyl | $OCH_3$ | O | |
| 4.8 | Phenyl | Methyl | Methyl | OH | O | |
| 4.9 | 4-Bromophenyl | Phenyl | Methyl | $OCH_3$ | O | 130–135 |
| 4.10 | 4-Bromophenyl | Phenyl | Methyl | OH | O | 155–160 |
| 4.11 | 2-Fluorophenyl | Phenyl | Methyl | $OCH_3$ | O | 128–134 |
| 4.12 | 2-Fluorophenyl | Phenyl | Methyl | OH | O | 170–171 |
| 4.13 | 3-Fluorophenyl | Phenyl | Methyl | $OCH_3$ | O | 85–90 |
| 4.14 | 3-Fluorophenyl | Phenyl | Methyl | OH | O | 167–169 |
| 4.15 | 4-Fluorophenyl | Phenyl | Methyl | $OCH_3$ | O | 115–116 |
| 4.16 | 4-Fluorophenyl | Phenyl | Methyl | OH | O | 122–125 |
| 4.17 | 4-Chlorophenyl | Phenyl | Methyl | $OCH_3$ | O | Oil |
| 4.18 | 4-Chlorophenyl | Phenyl | Methyl | OH | O | 94–98 |
| 4.19 | 4-Methylphenyl | Phenyl | Methyl | $OCH_3$ | O | 100–114 |
| 4.20 | 4-Methylphenyl | Phenyl | Methyl | OH | O | Oil |
| 4.21 | 4-Nitrophenyl | Phenyl | Methyl | $OCH_3$ | O | |
| 4.22 | 4-Nitrophenyl | Phenyl | Methyl | OH | O | |
| 4.23 | Phenyl | 2-Fluorophenyl | Methyl | $OCH_3$ | O | 130–132 |
| 4.24 | Phenyl | 2-Fluorophenyl | Methyl | OH | O | 194–195 |
| 4.25 | Phenyl | 3-Methoxyphenyl | Methyl | $OCH_3$ | O | Oil |
| 4.26 | Phenyl | 3-Methoxyphenyl | Methyl | OH | O | Oil |
| 4.27 | Phenyl | 4-i-Propylphenyl | Methyl | $OCH_3$ | O | |
| 4.28 | Phenyl | 4-i-Propylphenyl | Methyl | OH | O | |
| 4.29 | Phenyl | 4-Bromophenyl | Methyl | $OCH_3$ | O | 129–131 |
| 4.30 | Phenyl | 4-Bromophenyl | Methyl | OH | O | Oil |
| 4.31 | Phenyl | 2-Furyl | Methyl | $OCH_3$ | O | |
| 4.32 | Phenyl | 2-Furyl | Methyl | OH | O | |
| 4.33 | Phenyl | 3-Furyl | Methyl | $OCH_3$ | O | |
| 4.34 | Phenyl | 3-Furyl | Methyl | OH | O | |
| 4.35 | Phenyl | 2-Thienyl | Methyl | $OCH_3$ | O | |
| 4.36 | Phenyl | 2-Thienyl | Methyl | OH | O | |
| 4.37 | Phenyl | 3-Thienyl | Methyl | $OCH_3$ | O | |
| 4.38 | Phenyl | 3-Thienyl | Methyl | OH | O | |
| 4.39 | 3-Methylphenyl | Phenyl | Methyl | $OCH_3$ | O | 155 |
| 4.40 | 3-Methylphenyl | Phenyl | Methyl | OH | O | 100–101 |
| 4.41 | 4-i-Propyl-phenyl | Phenyl | Methyl | $OCH_3$ | O | 130–131 |
| 4.42 | 4-i-Propyl-phenyl | Phenyl | Methyl | OH | O | 230 |
| 4.43 | Phenyl | 4-Chlorophenyl | Methyl | $OCH_3$ | O | 143–144 |
| 4.44 | Phenyl | 4-Chlorophenyl | Methyl | OH | O | 90–92 |
| 4.45 | Phenyl | 2-Methylphenyl | Methyl | $OCH_3$ | O | 179–180 |
| 4.46 | Phenyl | 2-Methylphenyl | Methyl | OH | O | |
| 4.47 | 2-Methylphenyl | Phenyl | Methyl | $OCH_3$ | O | 95–114 |
| 4.48 | 2-Methylphenyl | Phenyl | Methyl | OH | O | 80–85 |
| 4.49 | Phenyl | 4-Methylphenyl | Methyl | $OCH_3$ | O | 110–112 |
| 4.50 | Phenyl | 4-Methylphenyl | Methyl | OH | O | 156–157 |
| 4.51 | Phenyl | 3-Methylphenyl | Methyl | $OCH_3$ | O | Oil |
| 4.52 | Phenyl | 3-Methylphenyl | Methyl | OH | O | 158–160 |
| 4.53 | 4-Methoxy-phenyl | Phenyl | Methyl | $OCH_3$ | O | 157–158 |
| 4.54 | 4-Methoxy-phenyl | Phenyl | Methyl | OH | O | 106–107 |
| 4.55 | Phenyl | 4-Fluorophenyl | Methyl | $OCH_3$ | O | 160–165 |
| 4.56 | Phenyl | 4-Fluorophenyl | Methyl | OH | O | 99–100 |
| 4.57 | 4-Methylthio-phenyl | Phenyl | Methyl | $OCH_3$ | O | 160–163 |
| 4.58 | 4-Methylthio-phenyl | Phenyl | Methyl | OH | O | 248–250 |
| 4.59 | 4-t-Butyl-phenyl | Phenyl | Methyl | $OCH_3$ | O | 106–110 |
| 4.60 | 4-t-Butyl-phenyl | Phenyl | Methyl | OH | O | 250 |
| 4.61 | Phenyl | Phenyl | Ethyl | $OCH_3$ | O | 115–117 |
| 4.62 | Phenyl | Phenyl | Ethyl | OH | O | 84–85 |

TABLE 4-continued

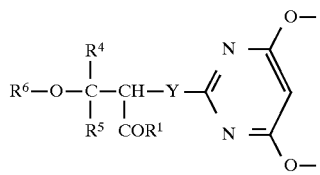

| Ex. No. | $R^6$ | $R^4$ | $R^5$ | $R^1$ | Y | M.p. [°C.] |
|---|---|---|---|---|---|---|
| 4.63 | 4-Acetoxy-phenyl | Phenyl | Methyl | $OCH_3$ | O | 157–159 |
| 4.64 | 4-Hydroxy-phenyl | Phenyl | Methyl | OH | O | 80–90 |

We claim:

1. A method of inhibiting endothelin receptors by administering to a patient a compound of the formula I

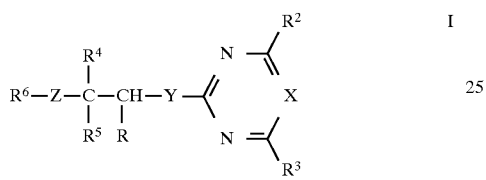

where R is formyl, $CO_2H$ or a radical which can be hydrolyzed to COOH, and the remaining substituents have the following meanings:

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{14}$ where $R^{14}$ is hydrogen or, together with $R^3$, forms a 3- or 4-membered alkylene or alkenylene chain in which, in each case, one methylene group is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $R^3$ is linked to $R^{14}$ as indicated above to form a 5- or 6-membered ring;

$R^4$ is $C_1$–$C_{10}$-alkyl which can carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxy-carbonyl, phenyl, phenoxy or phenylcarbonyl, where the phenyl radicals in turn can carry from one to five halogen atoms and/or from one to three of the following radicals: $C_1$–$C_4$-alkyl, C1–$C_4$-haloalkyl, $C_1$–$C_4$-alkoxy, C1–$C_4$-haloalkoxy and/or $C_1$–$C_4$-alkylthio; $C_1$–$C_4$-alkyl which can carry from one to five halogen atoms and carries one of the following radicals: a five-membered heteroaromatic ring which contains from one to three nitrogen atoms and/or one sulfur or oxygen atom and which can carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and/or phenyl; $C_3$–$C_{12}$-Cycloalkyl or $C_3$–$C_{12}$-cycloalkenyl, each of which can contain one oxygen or sulfur atom and can carry from one to five halogen atoms and/or one of the following radicals: $C_1$–$C_4$-alkyl, $C_1$–$C_4$-alkoxy, $C_1$–$C_4$-alkylthio, cyano, $C_1$–$C_8$-alkyl-carbonyl, carbonyl, $C_1$–$C_8$-alkoxycarbonyl, phenyl, phenoxy or phenyl-carbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio; $C_3$–$C_8$-alkenyl or $C_3C_6$-alkynyl, each of which can carry from one to five halogen atoms and/or one of the following radicals; $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

a five- or six-membered heteroaromatic ring which contains from one to three nitrogen atoms and/or one sulfur or oxygen atom and which can carry from one to four halogen atoms and/or one or two of the following radicals: $C_1$–$C_4$-alkyl, $C_{14}$-haloalkyl, $C_1$–$C_4$-alkoxy, $C_1$–$C_4$-haloalkoxy, CL-$c_4$-alkylthio, phenyl, phenoxy or phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, C1-$C_4$-haloalkoxy and/or $C_1$–$C_4$-alkylthio; phenyl or naphthyl, each of which can be substituted by one or more of the following radicals: halogen, nitro, cyano, hydroxyl, $C_1$–$C_4$-alkyl, $C_1$—$C_4$-haloalkyl, $C_{1–4}$-alkoxy, $C_1$–$C_4$-haloalkoxy, phenoxy, $C_1$–$C_4$-alkylthio, amino $C_1$–$C_4$-alkylamino or $C_1$–$C_4$-dialkylamino; $R^4$ and $R_5$ form, together with the adjacent carbon atom, a 3-membered membered ring which can contain one oxygen or sulfur atom and can carry from one to three of the following radicals: $C_1$–$C_4$-alkyl, halogen, $C_{1–4}$-haloalkyl, $C_1$–$C_4$-alkoxy, $C_1$–$C_4$-haloalkoxy and/or $C_1$–$C_4$-akylthio;

is hydrogen, $C_1$–$C_4$-alkyl, $C_3$–-alkenyl, $C_3$-alkynyl, $C_3$–$C_8$-Cycloalkyl, $C_4$–$C_4$-haloalkyl, $C_4$–$C_4$-alkoxyalkyl, $C_1$–$C_4$-alkylthioalkyl, phenyl or $R_5$ is linked to $R^4$ as indicated above to form a 3- to 8-membered ring; $R^6$ is $C_1$sufyl-alkyl, $C_3$–-alkenyl, $C_3$–-alkynyl or $C_3$–$C_8$-cycloalkyl, it being possible for each of these radicals to be substituted one or more times by: halogen, nitro, cyano, $C_1$–$C_4$-alkoxy, $C_3$–$C_6$-alkenyloxy, $C_3$–-alkynyloxy, $C_1$–$C_4$-alkyl-thio, $C_1$–$C_4$-haloalkoxy, $C_1$–$C_4$-alkylcarbonyl, $C_4$-alkoxy carbonyl, $C_1$–$C_4$-alkylamino, di-$C_1$–$C_4$-alkylamino, phenyl, phenoxy or phenyl which is substituted one or more times, e.g. from one to three times, by halogen, nitro, cyano, $C_1$–$C_4$-alkyl, $C_1$–$C_4$-haloalkyl, $C_1$–$C_4$-alkoxy, $C_4$-haloalkoxy or $C_1$–$C_4$-alkylthio;

phenyl or naphthyl, each of which can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1$–$C_4$-alkylamino or $C_1$–$C_4$-dialkylamino;

a five- or six-membered heteroaromatic ring which contains from one to three nitrogen atoms and/or one sulfur or oxygen atom and which can carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkyl thio, phenyl, phenoxy or phenylcarbonyl, where the phenyl radicals in turn can carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio; Y is sulfur or oxygen or a single bond; Z is sulfur or oxygen.

* * * * *

UNITED STATES PATENT AND TRADEMARK OFFICE
CERTIFICATE OF CORRECTION

PATENT NO. : 5,840,722

DATED : November 24, 1998

INVENTOR(S) : BAUMANN et al.

It is certified that error appears in the above-identified patent and that said Letters Patent is hereby corrected as shown below:

Col. 27, claim 1, line 42, ""$^6$-membered" should be --6-membered--;
  line 46, "alkoxy-carbonyl" should be --alkoxycarbonyl--;
  line 50, "C1-C$_4$-", both occurrences, should be --C$_1$-C$_4$- --;
  line 51, "C$_1$-C$_4$-alkyl" should be --C$_1$-C$_6$-alkyl--;
  line 60, "Cycloalkyl" should be --cycloalkyl--;
  line 64, "alkyl-carbonyl" should be --alkylcarbonyl--;
  line 65, delete "carbonyl,";
  line 66, "phenyl-carbonyl" should be --phenylcarbonyl--.
Col. 28, claim 1, line 21, "C$_3$-C$_8$-" should be --C$_3$-C$_6$- --;
  line 22, "C$_3$C$_6$-" should be --C$_3$-C$_6$- --;
  line 34, "C$_{14}$-" should be --C$_1$-C$_4$- --;
  line 35, CL-$_{C4}$-" should be --C$_1$-C$_4$- --;
  line 39, "Cl" should be --C$_1$--;
  line 45, after "amino" insert --,--;
  line 49, C$_1$-$_4$-" should be --C$_1$-C$_4$- --;
  line 52, insert --R$^5$-- before "is hydrogen";
  line 52, "C$_3$--alkenyl, C$_3$-alkynyl," should be --C$_3$-C$_6$-alkenyl, C$_3$-C$_6$-alkynyl,--;
  line 53, "Cycloalkyl" should be --cycloalkyl--;
  line 53, "C$_4$--C$_4$-", both occurrences, should be --C$_1$-C$_4$- --'
  line 57, "C$_1$sulfyl-alkyl" should be --C$_1$-C$_8$-alkyl--;
  line 57, "C$_3$--alkenyl, C$_3$--alkynyl," should be --C$_3$-C$_6$-alkenyl, C$_3$-C$_6$-alkynyl,--;
line 60, "C$_3$--" should read --C$_3$ -C$_6$- --

UNITED STATES PATENT AND TRADEMARK OFFICE
CERTIFICATE OF CORRECTION

PATENT NO. : 5,840,722
DATED : November 24,1998
INVENTOR(S) : Baumann et al.

It is certified that error appears in the above-identified patent and that said Letters Patent is hereby corrected as shown below:

line 61, "alkyl-thio" should be --alkylthio--;
line 62, "$C_4$-alkoxy carbonyl" should be --$C_1$-$C_4$-alkoxycarbonyl--;
line 67, "$C_4$-haloalkoxy" should be --$C_1$-$C_4$-haloalkoxy--.
Col. 30, claim 1, line 2, "alkyl thio" should be --alkylthio--.

Signed and Sealed this

Twenty-seventh Day of July, 1999

Attest:

Q. TODD DICKINSON

*Attesting Officer*    *Acting Commissioner of Patents and Trademarks*